(12) United States Patent
Chen et al.

(10) Patent No.: US 12,220,241 B2
(45) Date of Patent: Feb. 11, 2025

(54) ELECTRONIC DEVICE AND METHOD FOR SELECTING FEATURE OF ELECTROCARDIOGRAM

(71) Applicants: National Health Research Institutes, Miaoli County (TW); Chang Gung Memorial Hospital, Keelung, Keelung (TW); Acer Medical Inc., New Taipei (TW); Acer Incorporated, New Taipei (TW)

(72) Inventors: Jun-Hong Chen, New Taipei (TW); Chun-Hsien Li, New Taipei (TW); Yun-Hsuan Chan, New Taipei (TW); Ting-Fen Tsai, Miaoli County (TW); Chi-Hsiao Yeh, Keelung (TW)

(73) Assignees: National Health Research Institutes, Miaoli County (TW); Chang Gung Memorial Hospital, Keelung, Keelung (TW); Acer Medical Inc., New Taipei (TW); Acer Incorporated, New Taipei (TW)

( * ) Notice: Subject to any disclaimer, the term of this patent is extended or adjusted under 35 U.S.C. 154(b) by 857 days.

(21) Appl. No.: 17/233,573

(22) Filed: Apr. 19, 2021

(65) Prior Publication Data
US 2022/0202343 A1   Jun. 30, 2022

(30) Foreign Application Priority Data
Dec. 29, 2020   (TW) .................................. 109146617

(51) Int. Cl.
*A61B 5/352*   (2021.01)
*A61B 5/353*   (2021.01)
(Continued)

(52) U.S. Cl.
CPC .............. *A61B 5/352* (2021.01); *A61B 5/353* (2021.01); *A61B 5/36* (2021.01); *G06N 20/00* (2019.01); *G16H 30/20* (2018.01)

(58) Field of Classification Search
CPC ........... A61B 5/352; A61B 5/353; A61B 5/36; G16H 30/20; G06N 20/00
See application file for complete search history.

(56) References Cited

U.S. PATENT DOCUMENTS

2016/0135706 A1\*   5/2016   Sullivan ............... A61B 5/0533
                                                      600/509
2020/0260980 A1\*   8/2020   Liu ........................ A61B 5/352

FOREIGN PATENT DOCUMENTS

CN   105232027   1/2016
CN   107951485   4/2018
(Continued)

OTHER PUBLICATIONS

"Search Report of Europe Counterpart Application", issued on Nov. 16, 2021, pp. 1-7.
(Continued)

*Primary Examiner* — James M Kish
*Assistant Examiner* — Roland Dinga
(74) *Attorney, Agent, or Firm* — JCIPRNET

(57) ABSTRACT

An electronic device and a method for selecting a feature of an electrocardiogram (ECG) are provided. The method includes: obtaining the ECG; performing a first pre-processing on the ECG to generate a first ECG; marking multiple extreme points corresponding to at least one type of wave on the first ECG; calculating a first feature value corresponding to a first feature according to the multiple extreme points of the at least one type of wave, generating a first performance index corresponding to a machine learning model according to the first feature value, and determining whether to select the first feature according to the first performance index; and
(Continued)

outputting the first feature in response to selecting the first feature.

12 Claims, 7 Drawing Sheets

(51) Int. Cl.
    *A61B 5/36*  (2021.01)
    *G06N 20/00*  (2019.01)
    *G16H 30/20*  (2018.01)

(56) References Cited

FOREIGN PATENT DOCUMENTS

| | | |
|---|---|---|
| CN | 110013247 | 7/2019 |
| CN | 110141214 | 8/2019 |
| EP | 3692904 | 8/2020 |
| EP | 3698708 | 8/2020 |
| WO | 2018119316 | 6/2018 |

OTHER PUBLICATIONS

Feifei Liu et al., "Dynamic ECG Signal Quality Evaluation Based on the Generalized bSQI Index", Special Section on Advanced Information Sensing and Learning Technologies for Data-Centric Smart Health Applications, vol. 6, Aug. 2018, pp. 41892-41902.

* cited by examiner

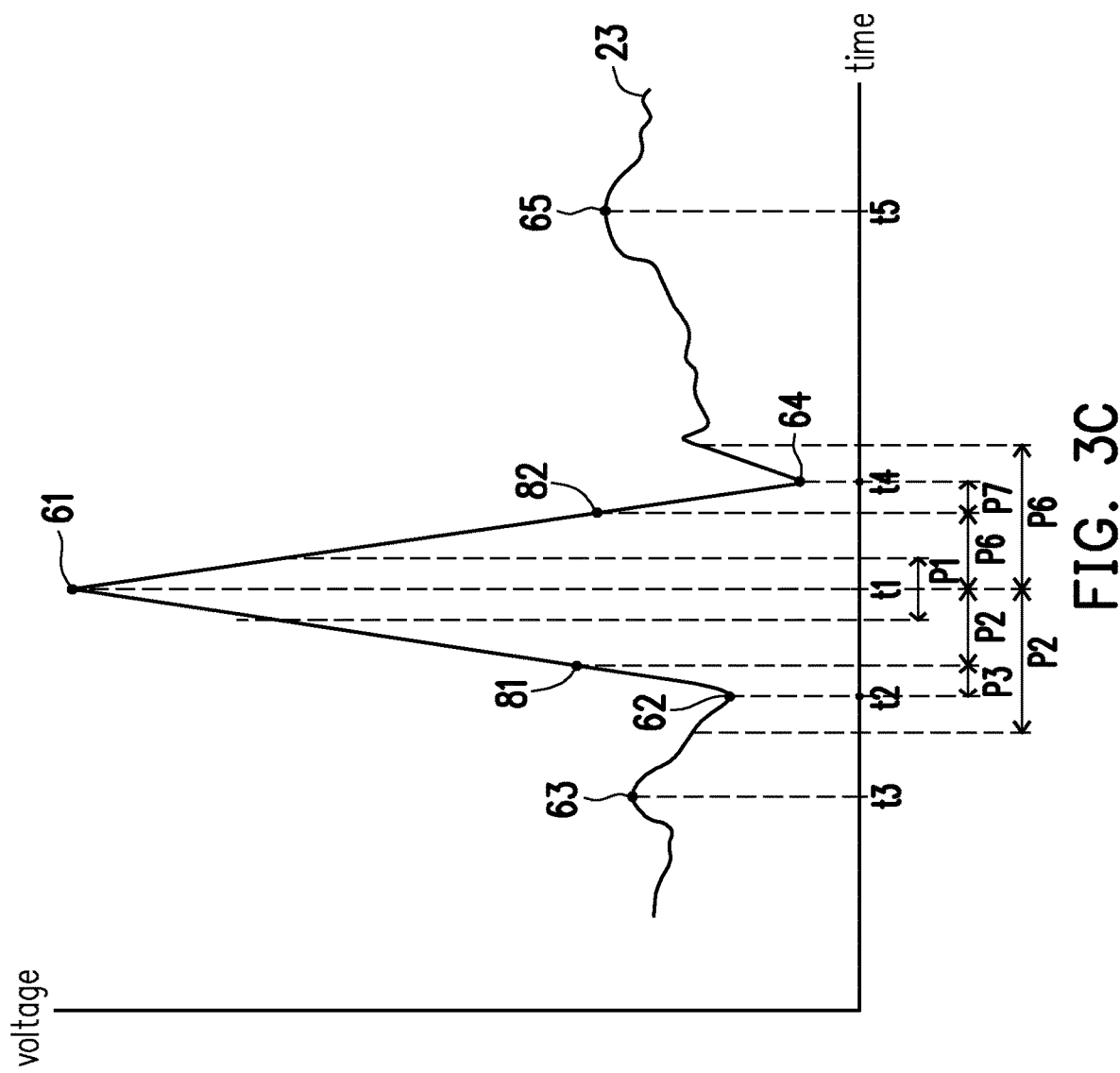

ELECTRONIC DEVICE AND METHOD FOR SELECTING FEATURE OF ELECTROCARDIOGRAM

CROSS-REFERENCE TO RELATED APPLICATION

This application claims the priority benefit of Taiwan application serial no. 109146617, filed on Dec. 29, 2020. The entirety of the above-mentioned patent application is hereby incorporated by reference herein and made a part of this specification.

BACKGROUND

Technical Field

The disclosure relates to an electronic device and a method for selecting a feature of an electrocardiogram (ECG).

Description of Related Art

Cardiovascular disease has been one of the top ten causes of death for many years. Since cardiovascular disease has no obvious symptoms, cardiovascular disease poses a great threat to patients. The walls of coronary arteries that supply blood to the heart may harden or become narrow due to factors such as aging, smoking damage, the three highs, genetics, or eating habits. In this way, blood supply to the heart may be insufficient, which may cause issues such as angina pectoris or myocardial infarction.

In order to examine coronary artery related diseases, doctors often use treadmill electrocardiogram for non-invasive examination. However, compared with the direct invasive examination method, the use of treadmill electrocardiogram for cardiovascular disease examination has the issue of excessive false positive (FP). Therefore, how to provide a method that can improve the performance of a machine learning model used to analyze an electrocardiogram is one of the goals for persons skilled in the art.

SUMMARY

The disclosure provides an electronic device and a method for selecting a feature of an electrocardiogram (ECG), which may find one or more features highly related to heart disease.

An electronic device for selecting a feature of an ECG of the disclosure includes a processor, a storage medium, and a transceiver. The storage medium stores multiple modules. The processor is coupled to the storage medium and the transceiver, and accesses and executes multiple modules. Multiple modules include a data collection module, a first pre-processing module, a marking module, a feature establishing module, a feature selection module, and an output module. The data collection module obtains the ECG through the transceiver. The first pre-processing module performs a first pre-processing on the ECG to generate a first ECG. The marking module marks multiple extreme points corresponding to at least one type of wave on the first ECG. The feature establishing module calculates a first feature value corresponding to a first feature according to the multiple extreme points of the at least one type of wave, and generates a first performance index corresponding to a machine learning model according to the first feature value. The feature selection module determines whether to select the first feature according to the first performance index. The output module outputs the first feature through the transceiver in response to selecting the first feature.

In an embodiment of the disclosure, the at least one type of wave includes an R wave. The multiple modules further include a second pre-processing module. The second pre-processing module performs a second pre-processing on the first ECG to generate a second ECG. The marking module divides the second ECG into multiple portions according to a window function, and marks a first data point with the maximum value in a first portion as a first reference point in response to the first portion in the multiple portions including at least one data point greater than zero. The first reference point corresponds to a first reference time point. The marking module determines a first period of the first ECG according to the first reference time point, and marks a second data point with the maximum value in the first period as a first R wave extreme point. The first reference time point is located at the center of the first period. Multiple extreme points include the first R wave extreme point.

In an embodiment of the disclosure, the at least one type of wave further includes a Q wave. The first R wave extreme point corresponds to a first time point. The marking module determines a second period of the first ECG according to the first time point, and marks a third data point with the minimum value in the second period as a first Q wave extreme point. The first time point is a latest time point of the second period. Multiple extreme points include the first Q wave extreme point.

In an embodiment of the disclosure, the marking module marks a fourth data point with the minimum value in a third period earlier than the second period as the first Q wave extreme point in response to the slope of the third data point being positive.

In an embodiment of the disclosure, the first Q wave extreme point corresponds to a second time point. The marking module marks multiple R wave extreme points including the first R wave extreme point on the first ECG, calculates an average RR interval according to multiple R wave extreme points, determines a weight according to the number of multiple R wave extreme points, and determines a second window function according to the average RR interval and the weight. The marking module determines a fourth period earlier than the second time point according to the second window function, and marks a fifth data point with the maximum value in the fourth period as a first P wave extreme point. The second time point corresponds to a second latest time point of the fourth period. Multiple extreme points include the first P wave extreme point.

In an embodiment of the disclosure, the marking module marks a sixth data point with the maximum value in a fifth period earlier than the fourth period as the first P wave extreme point in response to the slope of the fifth data point being negative.

In an embodiment of the disclosure, the first pre-processing includes the following step. Baseline wandering removal, noise removal, and standardization are performed on the ECG to generate the first ECG.

In an embodiment of the disclosure, the second pre-processing includes the following steps. The first ECG is divided into three portions. The three portions include a first period ECG, a second period ECG later than the first period ECG, and a third period ECG later than the second period ECG. The lengths of the first period ECG and the third period of ECG are the same. A first standard deviation corresponding to the first period ECG and a second standard deviation corresponding to the second period ECG are calculated. The first period ECG is deleted from the first ECG in response to a difference value between the first standard deviation and the second standard deviation being greater than a first threshold.

In an embodiment of the disclosure, the second pre-processing further includes the following steps. Wavelet transform is performed on the first ECG to generate a transformed ECG. The transformed ECG is standardized into a standard score. Multiple data points less than a second threshold in the standard score are set to zero to generate the second ECG.

In an embodiment of the disclosure, the data collection module receives multiple ECGs through the transceiver. Multiple ECGs include a first lead ECG and a second lead ECG. The data collection module standardizes the first lead ECG into a first standard score function, and selects at least one first standard score from multiple first standard scores of the first standard score function in response to at least one first absolute value of the at least one first standard score in the first standard score function being greater than a first absolute value of a first standard score in the first standard score function to calculate a first total. The data collection module standardizes the second lead ECG into a second standard score function, and selects at least one second standard score from multiple second standard scores of the second standard score function in response to at least one second absolute value of the at least one second standard score in the second standard score function being greater than a second absolute value of a second standard score in the second standard score function to calculate a second total. The data collection module selects the ECG corresponding to a third lead from multiple ECGs according to the signs of the first total and the second total.

In an embodiment of the disclosure, the first lead ECG corresponds to a lead I, the second lead ECG corresponds to a lead aVF, and the third lead corresponds to one of a lead II, a lead aVL, the lead aVF, and a lead aVR.

In an embodiment of the disclosure, the feature selection module selects the first feature in response to the first performance index being greater than a performance threshold.

In an embodiment of the disclosure, the feature establishing module calculates a second feature value corresponding to a second feature according to multiple extreme points of the at least one type of wave, and generates a second performance index corresponding to the machine learning model according to the second feature value. The feature selection module selects the first feature from the first feature and the second feature in response to the first performance index being greater than the second performance index.

A method for selecting a feature of an ECG of the disclosure includes the following steps. The ECG is obtained. A first pre-processing is performed on the ECG to generate a first ECG. Multiple extreme points corresponding to at least one type of wave are marked on the first ECG. A first feature value corresponding to a first feature is calculated according to the multiple extreme points of the at least one type of wave. A first performance index corresponding to a machine learning model is generated according to the first feature value. Whether to select the first feature is determined according to the first performance index. The first feature is output in response to selecting the first feature.

Based on the above, the disclosure may select one or more features that are highly related to heart disease from many features of the ECG and output the features to prompt the user. Therefore, the user may train the machine learning model with better performance according to the selected features of the disclosure. The machine learning model may be used to determine the health condition of coronary arteries of a test subject according to the ECG.

BRIEF DESCRIPTION OF THE DRAWINGS

FIG. 3C is a first partial enlarged view of a first electrocardiogram of FIG. 3B according to an embodiment of the disclosure.

DETAILED DESCRIPTION OF DISCLOSED EMBODIMENTS

Figure 1:
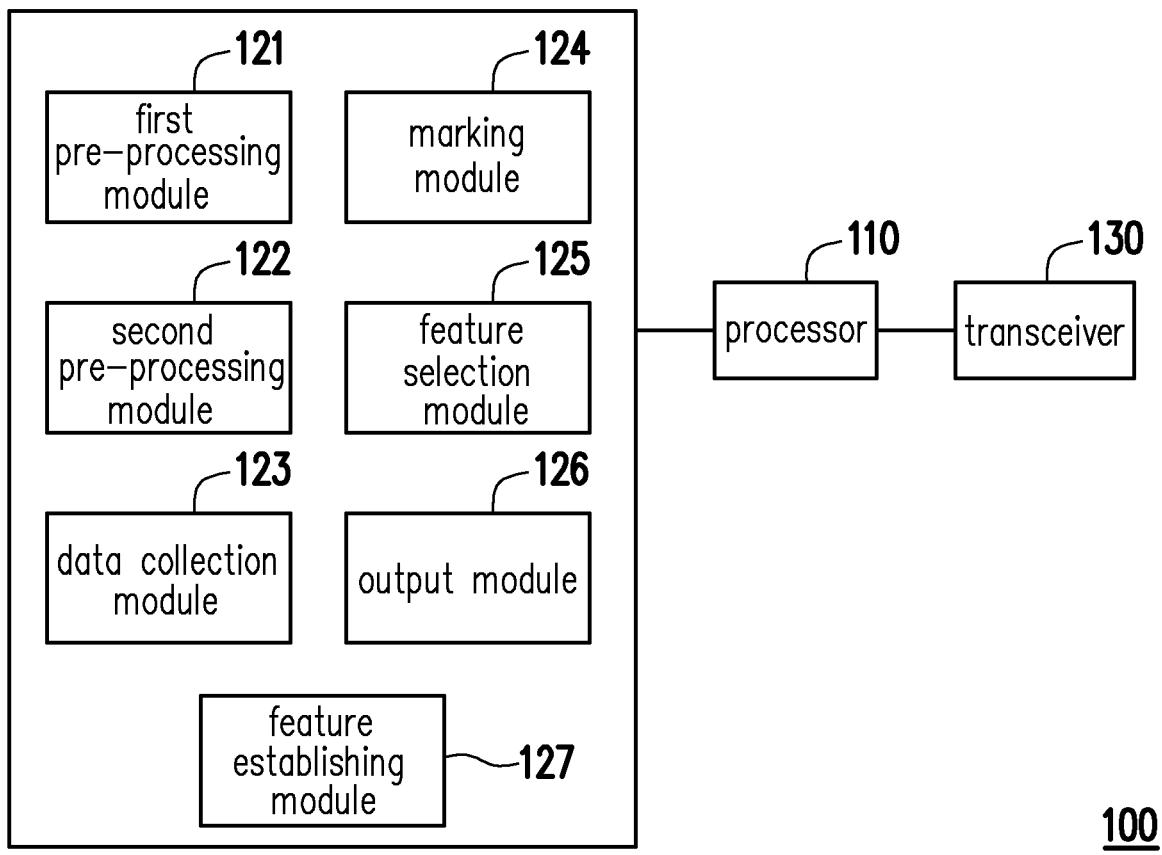
FIG. 1 is a schematic view of an electronic device for selecting a feature of an electrocardiogram according to an embodiment of the disclosure.

In order for the content of the disclosure to be more understandable, the following embodiments are specifically cited as examples on which the disclosure can be implemented. In addition, wherever possible, elements/components/steps with the same reference numerals in the drawings and embodiments represent the same or similar parts.

FIG. 1 is a schematic view of an electronic device 100 for selecting a feature of an electrocardiogram (ECG) according to an embodiment of the disclosure. The electronic device 100 may include a processor 110, a storage medium 120, and a transceiver 130.

The processor 110 is, for example, a central processing unit (CPU), other programmable general-purpose or specific-purpose micro control unit (MCU), microprocessor, digital signal processor (DSP), programmable controller, application specific integrated circuit (ASIC), graphics processing unit (GPU), image signal processor (ISP), image processing unit (IPU), arithmetic logic unit (ALU), complex programmable logic device (CPLD), field programmable gate array (FPGA), other similar elements, or a combination of the above elements. The processor 110 may be coupled to the storage medium 120 and the transceiver 130, and access and execute multiple modules and various applications stored in the storage medium 120.

The storage medium 120 is, for example, any type of fixed or removable random access memory (RAM), read-only memory (ROM), flash memory, hard disk drive (HDD), solid state drive (SSD), similar elements, or a combination of the above elements, which is used to store multiple modules or various applications that may be executed by the processor 110. In this embodiment, the storage medium 120 may store multiple modules including a first pre-processing module 121, a second pre-processing module 122, a data collection module 123, a marking module 124, a feature selection module 125, an output module 126, a feature establishing module 127, etc., and the functions thereof will be explained later.

The transceiver 130 transmits and receives signals in a wireless or wired manner. The transceiver 130 may also execute operations such as low noise amplification, impedance matching, frequency mixing, up or down frequency conversion, filtering, and amplification.

The data collection module 123 may receive multiple ECGs of a test subject through the transceiver 130. The multiple ECGs may respectively correspond to multiple leads. For example, multiple leads may include a lead I, a lead II, a lead III, a lead aVR, a lead aVL, a lead aVF, a lead V1, a lead V2, a lead V3, a lead V4, a lead V5, a lead V6, etc.

In order to select the feature from the ECG, the electronic device 100 may first mark extreme points of a P wave, a Q wave, an R wave, an S wave, or a T wave on the ECG. The extreme points include a wave peak or a wave trough. Since not all ECGs of the leads are suitable for marking extreme points, after obtaining multiple ECGs, the data collection module 123 may select an ECG corresponding to a primary lead (that is, primary ECG) from the multiple ECGs. The ECG may be used to mark the extreme points of waves.

Specifically, the data collection module 123 may select a lead I ECG and a lead aVF ECG from multiple ECGs. The data collection module 123 may standardize the lead I ECG into a first standard score function. Then, the data collection module 123 may select at least one first standard score from multiple first standard scores of the first standard score function in response to at least one first absolute value of the at least one first standard score in the first standard score function being greater than a first absolute value of a first standard score in the first standard score function to calculate a first total. For example, it is assumed that the first standard score function includes 100 first standard scores. The data collection module 123 may select 2 first standard scores (the absolute values of the 2 first standard scores are greater than the absolute values of the other 98 first standard scores) corresponding to the first 2% of absolute values from the first standard score function, and add the 2 first standard scores to calculate the first total.

Similarly, the data collection module 123 may standardize the lead aVF ECG into a second standard score function. Then, the data collection module 123 may select at least one second standard score from multiple second standard scores of the second standard score function in response to at least one second absolute value of the at least one second standard score in the second standard score function being greater than a second absolute value of a second standard score in the second standard score function to calculate a second total. For example, it is assumed that the second standard score function includes 100 second standard scores. The data collection module 123 may select 2 second standard scores (the absolute values of the 2 second standard scores are greater than the absolute values of the other 98 second standard scores) corresponding to the first 2% of absolute values from the second standard score function, and add the 2 second standard scores to calculate the second total.

After obtaining the first total and the second total, the data collection module 123 may select the primary lead according to the signs of the first total and the second total, so as to select the ECG corresponding to the primary lead from the multiple ECGs. Specifically, the data collection module 123 may determine the primary lead according to Table 1.

TABLE 1

| Sign of first total (lead I) | Sign of second total (lead aVF) | Primary lead |
|---|---|---|
| Positive | Positive | Lead II |
| Positive | Negative | Lead aVL |
| Negative | Positive | Lead aVF |
| Negative | Negative | Lead aVR |

Figure 2:
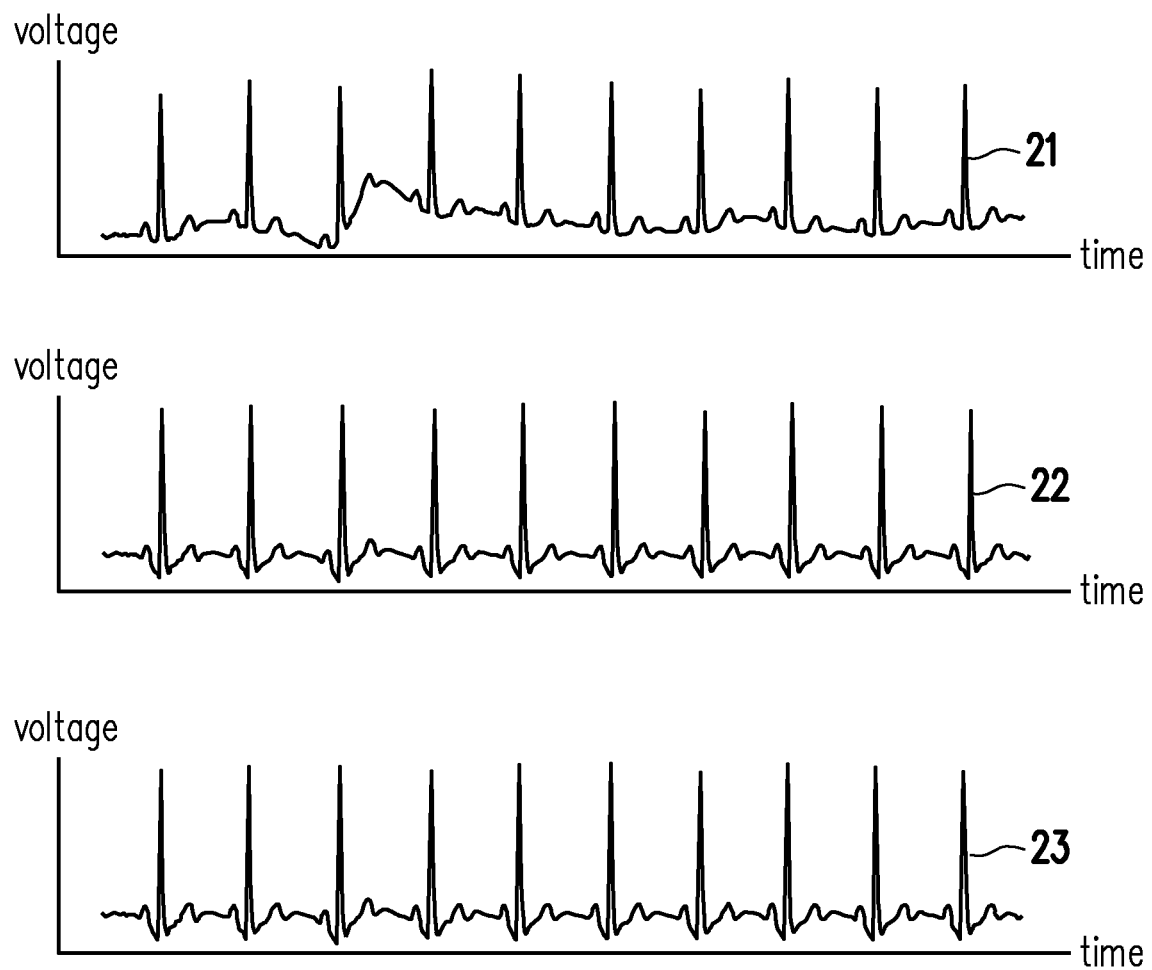
FIG. 2 is a schematic view of a first pre-processing according to an embodiment of the disclosure.

After selecting the ECG corresponding to the primary lead, the first pre-processing module 121 may perform the first pre-processing on the ECG to generate the first ECG. The first pre-processing may include steps such as baseline wandering removal, noise removal, or standardization, but the disclosure is not limited thereto. FIG. 2 is a schematic view of a first pre-processing according to an embodiment of the disclosure. The first pre-processing module 121 may perform the first pre-processing on an ECG 21 to generate a first ECG 23. The original signal of the ECG 21 may cause baseline wandering due to factors such as measurement environment or errors. Therefore, the first pre-processing module 121 may perform the baseline wandering removal on the ECG 21 through, for example, a band rejection filter or a notch filter to generate a more regular ECG 22. Then, the first pre-processing module 121 may perform the noise removal on the adjusted ECG 22 through, for example, a low-pass filter to smooth the ECG 22. Then, the first pre-processing module 121 may standardize the smoothed ECG 22 to generate the first ECG 23 with an average value of 0.

In an embodiment, before obtaining the primary lead, the first pre-processing module 121 may first perform the first pre-processing on the multiple ECGs collected by the data collection module 123 and respectively corresponding to the multiple leads, and determine the primary lead according to the multiple ECGs after the first pre-processing.

Figure 3A:
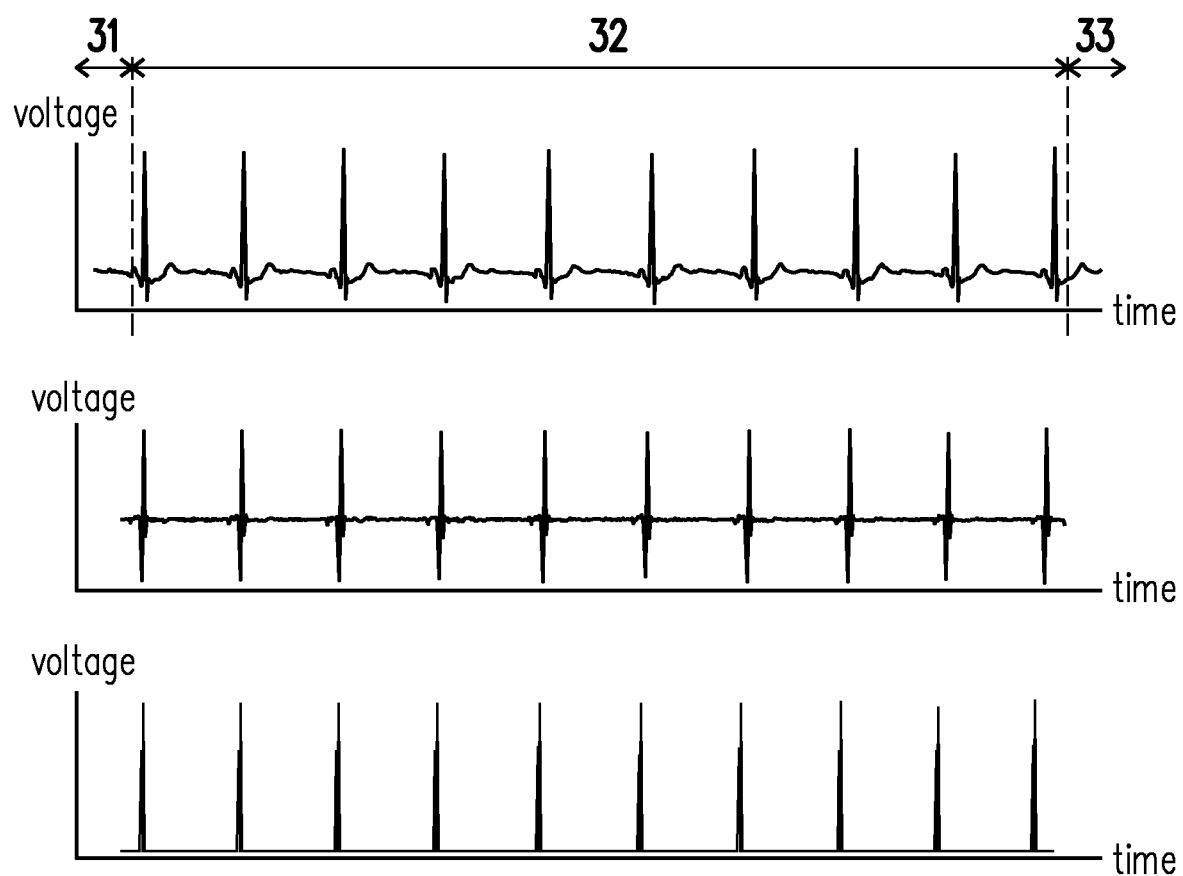
FIG. 3A is a schematic view of a second pre-processing according to an embodiment of the disclosure.

After obtaining the first ECG 23, the second pre-processing module 122 may perform a second pre-processing on the first ECG 23 to generate a second ECG 25. FIG. 3A is a schematic view of a second pre-processing according to an embodiment of the disclosure. The measurement signal of the ECG is often disturbed by noise at the beginning or end of the measurement, which causes distortion. Therefore, the second pre-processing module 122 may remove a head portion and a tail portion of the first ECG 23. Specifically, the second pre-processing module 122 may divide the first ECG 23 into three portions. The three portions may include a first period ECG 31, a second period ECG 32 later than the first period ECG 31, and a third period ECG 33 later than the second period ECG 32. The lengths of the first period ECG 31 and the third period ECG 33 are the same. Specifically, if the first period ECG 31 accounts for m % (where m is a positive real number) of the first ECG 23, then the third period ECG 33 may account for m % of the first ECG 23, and the second period ECG 32 may account for (1−2*m) % of the first ECG 23. For example, if the first period ECG 31 accounts for 10% of the first ECG 23, then the third period ECG 33 may account for 10% of the first ECG 23, and the second period ECG 32 may account for 80% of the first ECG 23.

Then, the second pre-processing module 122 may calculate a standard deviation corresponding to each period of the ECG. The second pre-processing module 122 may calculate a first standard deviation corresponding to the first period ECG 31 (or a third standard deviation corresponding to the third period ECG 33) and a second standard deviation corresponding to the second period ECG 32. If a difference value between the first standard deviation (or the third standard deviation) and the second standard deviation is greater than a first threshold, then the second pre-processing module 122 may delete the first period ECG 31 (or the third period ECG 33) from the first ECG 23, thereby removing the head portion and the tail portion of the first ECG 23. The first threshold may be adjusted by the user according to requirements.

In order for the extreme points of the waveform of the ECG to be more prominent for marking, the second pre-processing module 122 may further perform wavelet transform on the first ECG 23 to generate a transformed ECG 24. The second pre-processing module 122 may standardize the transformed ECG 24 into a standard score, and set multiple data points less than a second threshold in the standard score to 0 to generate the second ECG 25. The second threshold may be adjusted by the user according to requirements. For example, the second threshold may be configured as X times the standard deviation of the standard score, where X may be a positive real number.

The marking module 124 may use the second ECG 25 as a reference to mark an R wave extreme point (that is, R wave peak) on the first ECG 23. Specifically, after generating the second ECG 25, the marking module 124 may determine a window function according to the second ECG 25. For example, the marking module 124 may calculate a window function W1 according to Equation (1), where mbpm is the maximum heart rate (in beats per minute, bpm), and SR is the sample rate of the ECG, and mbpm may be adjusted by the user according to requirements.

$$W1 = \left(\frac{60}{mbpm}\right) * SR \quad (1)$$

Figure 3B:
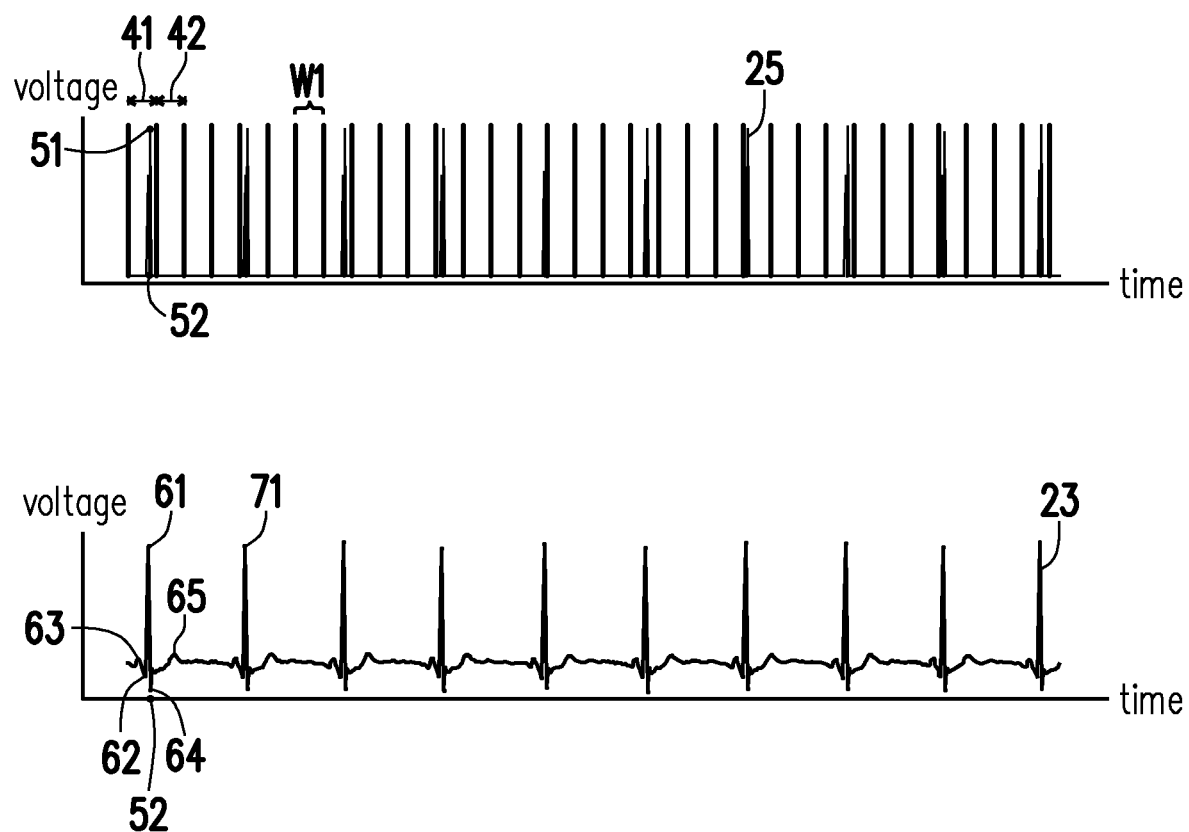
FIG. 3B is a schematic view of marking extreme points of various types of waves of an electrocardiogram according to an embodiment of the disclosure.

The marking module 124 may divide the second ECG 25 into multiple portions according to the window function W1, and mark a data point with the maximum value in a portion in the multiple portions the portion as a reference point in response to the portion including at least one data point greater than zero. The reference point corresponds to a reference time point. FIG. 3B is a schematic view of marking extreme points of various types of waves of an ECG according to an embodiment of the disclosure. For example, the marking module 124 may divide the second ECG 25 into multiple portions including a portion 41 and a portion 42 according to the window function W1. The marking module 124 may mark the data point with the maximum value in the portion 41 as a reference point 51 in response to the portion 41 including multiple data points greater than zero. The reference point 51 may correspond to a reference time point 52. Relatively speaking, since portion 42 does not include any data point greater than zero, the marking module 124 will not mark any reference point in the portion 42.

In an embodiment, the marking module 124 may filter multiple reference points with distances that are too close. For example, the marking module 124 may pre-store the minimum allowable distance. If the distance between two reference points is less than the minimum allowable distance, the marking module 124 may delete the reference point with the smaller value of the two reference points. The minimum allowable distance may be defined by the user according to requirements. For example, the user may determine the minimum allowable distance according to an RR interval of people who do not have coronary artery disease.

After marking the reference point on the second ECG 25, the marking module 124 may mark multiple extreme points of at least one type of wave on the first ECG 23 according to the reference time point corresponding to the reference point. The at least one type of wave may include a P wave, a Q wave, an R wave, an S wave, or a T wave. The multiple extreme points may include the wave peak of the P wave, the wave trough of the Q wave, the wave peak of the R wave, the wave trough of the S wave, or the wave peak of the T wave.

FIG. 3C is a first partial enlarged view of the first ECG 23 of FIG. 3B according to an embodiment of the disclosure. The marking module 124 may determine a period P1 of the first ECG 23 according to the reference time point 52. The reference time point 52 may be located at the center of the period P1. For example, the earliest time point in the period P1 may be the reference time point 52 minus k seconds, and the latest time point in the period P1 may be the reference time point 52 plus k seconds, where k may be a positive real number. The marking module 124 may mark a data point with the maximum value in the period P1 as an R wave extreme point 61. The R wave extreme point 61 corresponds to the wave peak of the R wave.

After determining the position of the R wave extreme point 61 on the first ECG 23, the marking module 124 may mark a Q wave extreme point 62 according to the R wave extreme point 61. The R wave extreme point 61 and the Q wave extreme point 62 correspond to the same heartbeat. Specifically, if the R wave extreme point 61 corresponds to a time point t1, then the marking module 124 may determine a period P2 of the first ECG 23 according to the time point t1. The time point t1 may be the latest time point of the period P2. For example, the earliest time point of the period P2 may be the time point t1 minus i seconds, and the latest time point of the period P2 may be the time point t1, where i may be a positive real number. Persons skilled in the medical field often set i as 0.1. The marking module 124 may mark a data point with the minimum value in the period P2 as a Q wave extreme point 62. The Q wave extreme point 62 may be the wave trough of the Q wave.

In some cases, the period P2 may not include the Q wave extreme point 62. In this way, the above method may cause the marking module 124 to mistakenly mark the data point (for example, data point 81) at the edge of the period P2 as the Q wave extreme point. Therefore, in an embodiment, the marking module 124 may calculate the slope of the data point 81 with the minimum value in the period P2. If the slope of the data point 81 is positive, the marking module 124 may mark a data point with the minimum value in a period P3 as the Q wave extreme point 62. The period P3 is earlier than the period P2.

On the other hand, the marking module 124 may mark an S wave extreme point 64 according to the R wave extreme point 61. The R wave extreme point 61 and the S wave extreme point 64 correspond to the same heartbeat. Specifically, if the R wave extreme point 61 corresponds to the time point t1, the marking module 124 may determine a period P6 of the first ECG 23 according to the time point t1. The time point t1 may be the earliest time point of the period P6. For example, the earliest time point of the period P6 may be the time point t1, and the latest time point of the period P6 may be the time point t1 plus i seconds, where i may be a positive real number. Persons skilled in the medical field often set i as 0.1. The marking module 124 may mark a data point with the minimum value in the period P6 as the S wave extreme point 64. The S wave extreme point 64 may be the wave trough of the S wave.

In some cases, the period P6 may not include the S wave extreme point 64. In this way, the above method may cause the marking module 124 to mistakenly mark the data point (for example, data point 82) at the edge of the period P6 as the S wave extreme point. Therefore, in an embodiment, the marking module 124 may calculate the slope of the data point 82 with the minimum value in the period P6. If the slope of the data point 82 is negative, the marking module 124 may mark a data point with the minimum value in a period P7 as the S wave extreme point 64. The period P7 is later than the period P6.

Figure 3D:
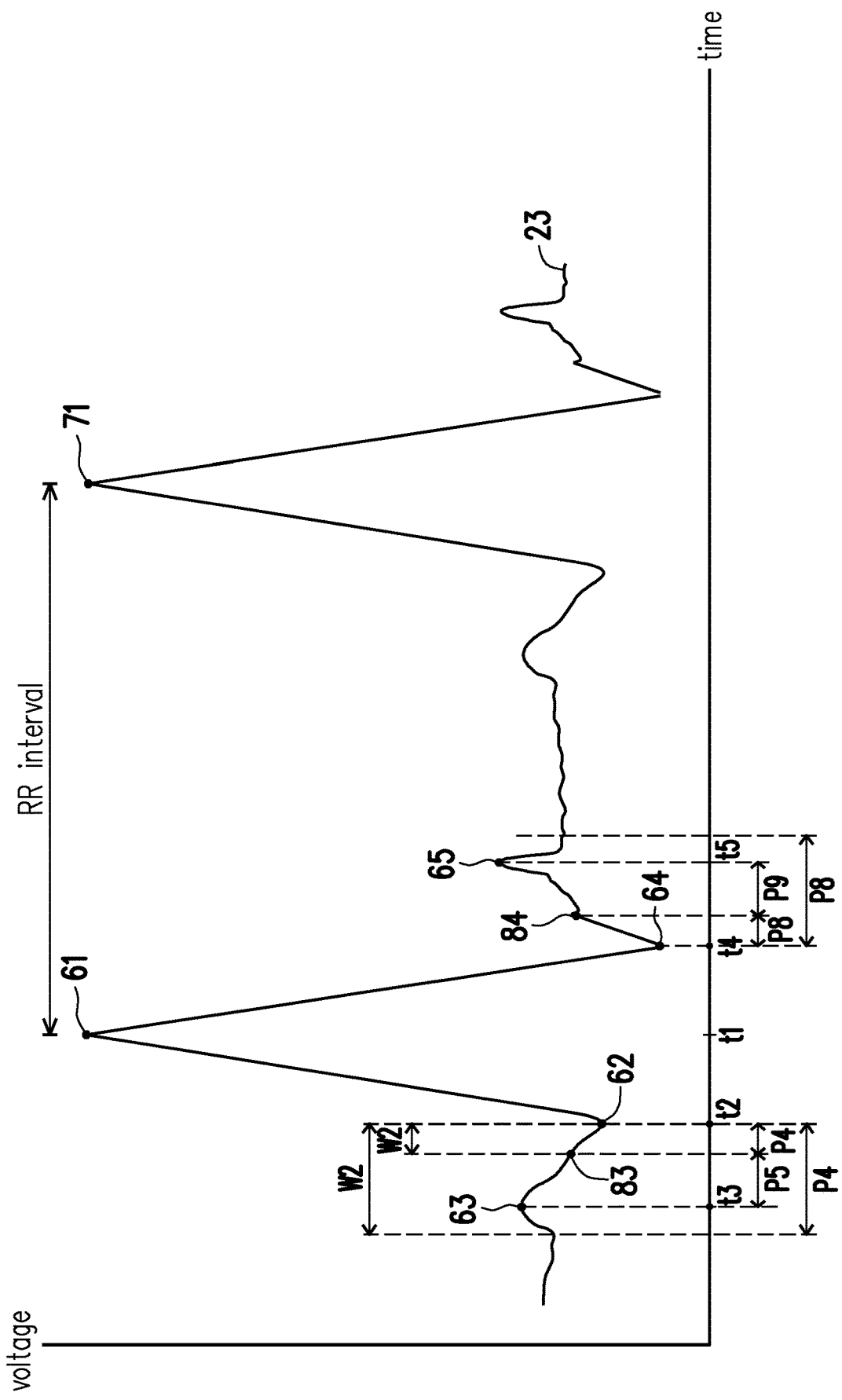
FIG. 3D is a second partial enlarged view of the first electrocardiogram of FIG. 3B according to an embodiment of the disclosure.

After marking the Q wave extreme point 62 and the S wave extreme point 64, the marking module 124 may obtain a time point t2 corresponding to the Q wave extreme point 62 and a time point t4 corresponding to the S wave extreme point 64. The marking module 124 may mark a P wave extreme point 63 according to the time point t2, and may mark a T wave extreme point 65 according to the time point t4. FIG. 3D is a second partial enlarged view of the first ECG 23 of FIG. 3B according to an embodiment of the disclosure. The marking module 124 may mark all R wave extreme points including the R wave extreme point 61 and the R wave extreme point 71 on the first ECG 23, and calculate the average RR interval according to all the R wave extreme points. The RR interval is the interval between adjacent R wave extreme points. FIG. 3D shows the RR interval between the R wave extreme point 61 and the R wave extreme point 71. The marking module 124 may calculate an average RR interval RRI according to Equation (2), where p is the number of R wave extreme points (for example, according to FIG. 3B, p corresponding to the first ECG 23 is equal to 10) of the first ECG and $R_j$ is the index of an R wave extreme point (for example, $R_1$ may represent the R wave extreme point 61 and $R_2$ may represent the R wave extreme point 71).

$$RRI = \frac{1}{p} \cdot \sum_{j=2}^{p} R_j - R_{j-1} \quad (2)$$

The marking module 124 may determine a weight PT according to the number p of multiple R wave extreme points in the first ECG 23, as shown in Equation (3), where S1 and S2 are positive numbers that may be defined by the user. For example, if p is equal to 10, S2 is greater than or equal to 10, and 10 is greater than or equal to S1, then the weight PT is equal to 3 (that is, 3.5−0.05*10=3).

$$PT = \begin{cases} 2, & \text{if } p < S1 \\ 3.5 - 0.05 * p, & \text{if } S1 \leq p \leq S2 \\ 3, & \text{if } p > S2 \end{cases} \quad (3)$$

The marking module 124 may determine a window function W2 according to the weight PT and the average RR interval RRI, as shown in Equation (4).

$$W2 = RRI/PT \quad (4)$$

After determining the window function W2, the marking module 124 may determine a period P4 earlier than the time point t2 corresponding to the Q wave extreme point 62 according to the window function W2. For example, the latest time point of the period P4 may be the time point t2, and the earliest time point of the period P4 may be the time point t2 minus the window function W2. After determining the period P4, the marking module 124 may mark a data point with the maximum value in the period P4 as the P wave extreme point 63.

In some cases, the period P4 may not include the P wave extreme point 63. In this way, the above method may cause the marking module 124 to mistakenly mark the data point (for example, data point 83) at the edge of the period P4 as the P wave extreme point. Therefore, in an embodiment, the marking module 124 may calculate the slope of the data point 83 with the minimum value in the period P4. If the slope of the data point 83 is negative, the marking module 124 may mark a data point with the maximum value in a period P5 as the P wave extreme point 63. The period P5 is earlier than the period P4.

On the other hand, the marking module 124 may determine a period P8 later than the time point t4 corresponding to the S wave extreme point 64 according to the window function W2. For example, the earliest time point of the period P8 may be the time point t4, and the latest time point of the period P8 may be the time point t4 plus the window function W2. After determining the period P8, the marking module 124 may mark a data point with the maximum value in the period P8 as the T wave extreme point 65.

In some cases, the period P8 may not include the T wave extreme point 65. In this way, the above method may cause the marking module 124 to mistakenly mark the data point (for example, data point 84) at the edge of the period P8 as the T wave extreme point. Therefore, in an embodiment, the marking module 124 may calculate the slope of the data point 84 with the minimum value in the period P8. If the slope of the data point 84 is positive, the marking module 124 may mark a data point with the maximum value in a period P9 as the T wave extreme point 65. The period P9 is later than the period P8.

After marking multiple extreme points (for example, the P wave extreme point, the Q wave extreme point, the R wave extreme point, the S wave extreme point, or the T wave extreme point) on the first ECG 23, the feature establishing module 127 may calculate multiple feature values respectively corresponding to multiple features according to the multiple extreme points. The multiple features (or the multiple feature values) may be associated with combinations of Field 1, Field 2, and Field 3 as shown in Table 2 or Table 3. Table 2 is associated with the features of a single heartbeat, and Table 3 is associated with the features of multiple heartbeats. For example, it can be seen from Table 2 that multiple features may include features corresponding to "the maximum value of a PQ interval", "the average value of a cosine value of an angle PQR", etc. For another example, it can be seen from Table 3 that multiple features may include a feature corresponding to "the standard deviation of a PP interval".

TABLE 2

| Field 1 | Field 2 | Field 3 |
|---|---|---|
| PQ | Interval | Maximum value |
| PR | Voltage | Minimum value |
| PS | Slope | Average value |
| PT | Area Under Line | Standard deviation |
| QR | | Range (maximum value-minimum value) |
| QS | | First quartile Q1 |
| QT | | Second quartile Q2 |
| RS | | Third quartile Q3 |
| RT | | Entropy |
| ST | | |
| PQR | Angle | Maximum value |
| PQS | Sine | Minimum value |

TABLE 2-continued

| Field 1 | Field 2 | Field 3 |
|---|---|---|
| PQT | Cosine | Average value |
| PRS | Tangent | Standard deviation |
| PRT | | Range (maximum value-minimum value) |
| PST | | First quartile Q1 |
| QRS | | Second quartile Q2 |
| QRT | | Third quartile Q3 |
| QST | | Entropy |
| RST | | |

TABLE 3

| Field 1 | Field 2 | Field 3 |
|---|---|---|
| PP | Interval | Maximum value |
| QQ | Voltage | Minimum value |
| RR | | Average value |
| SS | | Standard deviation |
| TT | | Range (maximum value-minimum value) |
| | | First quartile Q1 |
| | | Second quartile Q2 |
| | | Third quartile Q3 |
| | | Entropy |

The feature selection module 125 may select one or more features from multiple features, and determine a performance index of each feature on a machine learning model, thereby determining how to select the feature. The machine learning model may include, but is not limited to, a random forest (RF) model, a support vector machine (SVM) model, a least absolute shrinkage and selection operator (Lasso) model, a recursive feature elimination with cross validation (RFECV) model, or a statistical test model. The statistical test model may be associated with a chi-square test or an analysis of variance (ANOVA). The performance index may correspond to parameters, such as accuracy (ACC), precision, recall rate, false positive (FP), or F1 score, in a confusion matrix.

Taking a first feature in the multiple features as an example, the feature establishing module 127 may generate a first performance index corresponding to the machine learning model according to a first feature value of the first feature. Specifically, the feature selection module 125 may use data including the first feature to train the machine learning model, and test the performance of the machine learning model to generate the first performance index. Similarly, the feature establishing module 127 may generate multiple performance indexes respectively corresponding to multiple features. The multiple performance indexes may include the first performance index corresponding to the first feature, a second performance index corresponding to a second feature, a third performance index corresponding to a third feature, and so on.

The feature selection module 125 may determine whether to select the first feature according to the first performance index. If the feature selection module 125 determines to select the first feature, the output module 126 may output the first feature through the transceiver 130 as a reference for the user.

In an embodiment, the feature selection module 125 may determine to select the first feature in response to the first performance index being greater than a performance threshold. The performance threshold may be defined by the user according to requirements. For example, the feature selection module 125 may generate an "accuracy" corresponding to the feature of "the maximum value of the PQ interval". If the "accuracy" is greater than the preset performance threshold of "90%", the feature selection module 125 may select the feature of "the maximum value of the PQ interval".

In an embodiment, the feature selection module 125 may select the first feature from the first feature and the second feature in response to the first performance index corresponding to the first feature being greater than the second performance index corresponding to the second feature. In other words, the feature selection module 125 may select several features corresponding to higher performance indexes. For example, the feature establishing module 127 may generate a "first precision" corresponding to the feature of "the maximum value of the PQ interval", a "second precision" corresponding to the feature of "the average value of the cosine value of the angle PQR", and a "third precision" corresponding to the feature of "the standard deviation of the PP interval". If the feature selection module 125 intends to select a feature corresponding to the first 66.67% of precision, the feature selection module 125 may select "the maximum value of the PQ interval" from the feature of "the maximum value of the PQ interval" and the feature of "the standard deviation of the PP Interval" in response to the "first precision" being greater than the "third precision", and select "the average value of the cosine value of the angle PQR" from the feature of "the average value of the cosine value of the angle PQR" and the feature of "the standard deviation of the PP interval" in response to the "second precision" being greater than the "third precision".

Figure 4:
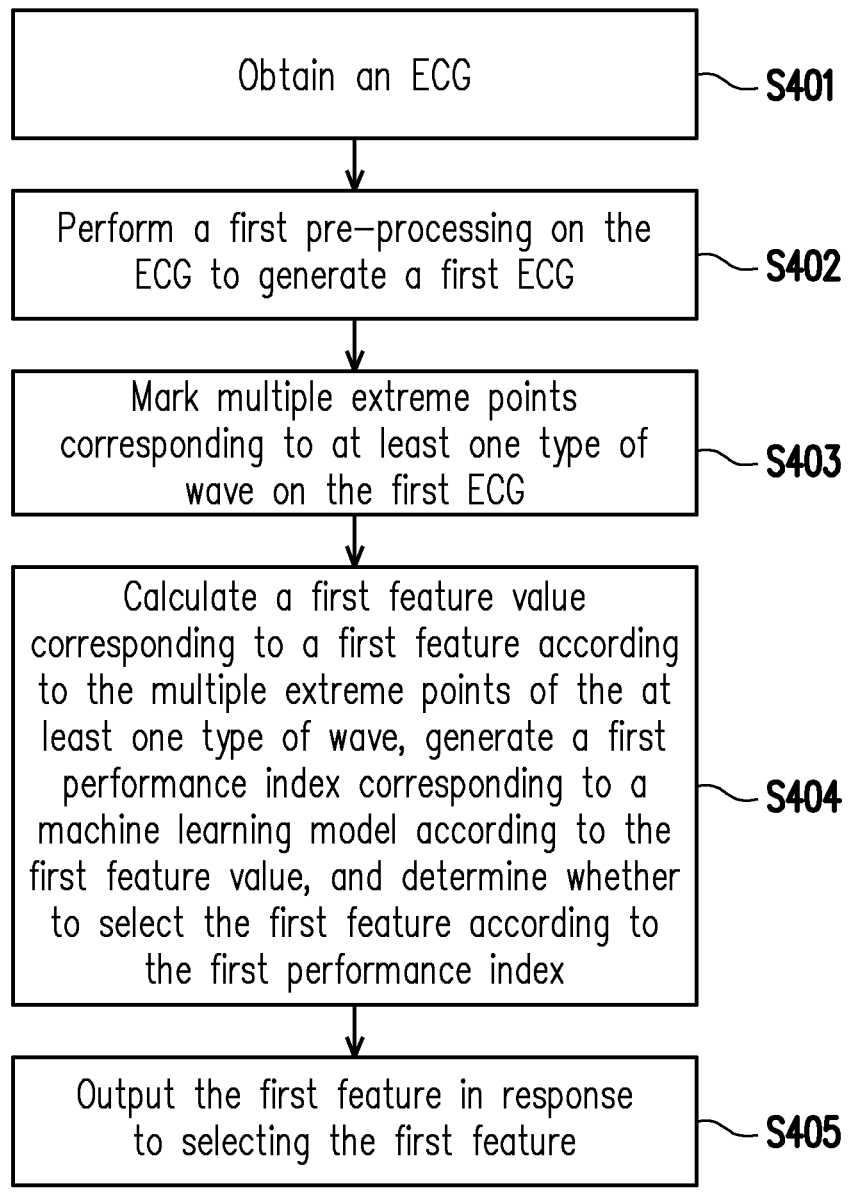
FIG. 4 is a flowchart of a method for selecting a feature of an electrocardiogram according to an embodiment of the disclosure.

FIG. 4 is a flowchart of a method for selecting a feature of an ECG according to an embodiment of the disclosure. The method may be implemented by the electronic device 100 shown in FIG. 1. In Step S401, the ECG is obtained. In Step S402, a first pre-processing is performed on the ECG to generate a first ECG. In Step S403, multiple extreme points corresponding to at least one type of wave are marked on the first ECG. In Step S404, a first feature value corresponding to a first feature is calculated according to the multiple extreme points of the at least one type of wave, a first performance index corresponding to a machine learning model is generated according to the first feature value, and whether to select the first feature is determined according to the first performance index. In Step S405, the first feature is output in response to selecting the first feature.

In summary, the disclosure may select one or more features that are highly related to heart disease from many features of the ECG. After obtaining multiple ECGs respectively corresponding to different leads, the disclosure may determine the ECG of which type of lead is more suitable for selecting the feature according to the ECG corresponding to the lead I and the ECG corresponding to the lead aVF. The disclosure may perform the first pre-processing on the ECG to generate the first ECG with relatively regular and smooth signals. In order to reduce the signal range difference between different patients, the disclosure may convert the first ECG into the form of a standard score to generate the second ECG. The disclosure may use the second ECG to accurately mark the wave peak of the R wave on the first ECG, thereby marking the wave peak or the wave trough of the P wave, the Q wave, the S wave, and the T wave according to the wave peak of the R wave. After obtaining multiple extreme points of various types of waves, the disclosure may calculate the feature value of a specific feature according to the multiple extreme points, and determine whether the specific feature can improve the performance of the machine learning model according to the feature value. If it is considered that the specific feature may significantly improve the performance of the machine learning model, the disclosure may output the specific feature to prompt the user. Therefore, the user may train a machine learning model with better performance according to the selected features of the disclosure. The machine learning model may be used to determine the health condition of coronary arteries of the test subject according to the ECG.

What is claimed is:

1. An electronic device for selecting a feature of an electrocardiogram, comprising:
    a transceiver;
    a storage medium, storing a plurality of modules; and
    a processor, coupled to the storage medium and the transceiver, and accessing and executing the plurality of modules, wherein the plurality of modules comprise:
    a data collection module, obtaining the electrocardiogram through the transceiver;
    a first pre-processing module, performing a first pre-processing on the electrocardiogram to generate a first electrocardiogram;
    a second pre-processing module, performing a second pre-processing on the first electrocardiogram to generate a second electrocardiogram;
    a marking module, marking a plurality of extreme points corresponding to at least one type of wave comprising an R wave on the first electrocardiogram by: dividing the second electrocardiogram into a plurality of portions according to a window function; marking a data point with a maximum value in a first portion in the plurality of portions as a first reference point in response to the first portion comprising at least one data point greater than zero, wherein the first reference point corresponds to a first reference time point; determining a first period of the first electrocardiogram according to the first reference time point; and marking a second data point with a maximum value in the first period as a first R wave extreme point, wherein the first reference time point is located at a center of the first period, wherein the plurality of extreme points comprise the first R wave extreme point;
    a feature establishing module, calculating a first feature value corresponding to a first feature according to the plurality of extreme points of the at least one type of wave, and generating a first performance index corresponding to a machine learning model according to the first feature value;
    a feature selection module, determining whether to select the first feature according to the first performance index; and
    an output module, outputting the first feature through the transceiver in response to selecting the first feature.

2. The electronic device according to claim 1, wherein the at least one type of wave further comprises a Q wave, wherein the first R wave extreme point corresponds to a first time point, wherein
    the marking module determines a second period of the first electrocardiogram according to the first time point, and marks a third data point with a minimum value in the second period as a first Q wave extreme point, wherein the first time point is a latest time point of the second period, wherein the plurality of extreme points comprise the first Q wave extreme point.

3. The electronic device according to claim 2, wherein the marking module marks a fourth data point with a minimum value in a third period earlier than the second period as the first Q wave extreme point in response to a slope of the third data point being positive.

4. The electronic device according to claim 2, wherein the first Q wave extreme point corresponds to a second time point, wherein
    the marking module marks a plurality of R wave extreme points comprising the first R wave extreme point on the first electrocardiogram, calculates an average RR interval according to the plurality of R wave extreme points, determines a weight according to a number of the plurality of R wave extreme points, and determines a second window function according to the average RR interval and the weight, wherein
    the marking module determines a fourth period earlier than the second time point according to the second window function, and marks a fifth data point with a maximum value in the fourth period as a first P wave extreme point, wherein the second time point corresponds to a second latest time point of the fourth period, wherein the plurality of extreme points comprise the first P wave extreme point.

5. The electronic device according to claim 4, wherein
    the marking module marks a sixth data point with a maximum value in a fifth period earlier than the fourth period as the first P wave extreme point in response to a slope of the fifth data point being negative.

6. The electronic device according to claim 1, wherein the first pre-processing comprises:
    performing baseline wandering removal, noise removal, and standardization on the electrocardiogram to generate the first electrocardiogram.

7. The electronic device according to claim 1, wherein the second pre-processing comprises:
    dividing the first electrocardiogram into three portions, wherein the three portions comprise a first period electrocardiogram, a second period electrocardiogram later than the first period electrocardiogram, and a third period electrocardiogram later than the second period electrocardiogram, wherein lengths of the first period electrocardiogram and the third period electrocardiogram are the same;
    calculating a first standard deviation corresponding to the first period electrocardiogram and a second standard deviation corresponding to the second period electrocardiogram; and
    deleting the first period electrocardiogram from the first electrocardiogram in response to a difference value between the first standard deviation and the second standard deviation being greater than a first threshold.

8. The electronic device according to claim 7, wherein the second pre-processing further comprises:
    performing wavelet transform on the first electrocardiogram to generate a transformed electrocardiogram;
    standardizing the transformed electrocardiogram into a standard score; and
    setting a plurality of data points less than a second threshold in the standard score to zero to generate the second electrocardiogram.

9. The electronic device according to claim 1, wherein
    the data collection module receives a plurality of electrocardiograms through the transceiver, wherein the plurality of electrocardiograms comprise a first lead electrocardiogram and a second lead electrocardiogram, wherein
    the data collection module standardizes the first lead electrocardiogram into a first standard score function, and selects at least one first standard score from a plurality of first standard scores of the first standard score function in response to at least one first absolute value of the at least one first standard score in the first standard score function being greater than a first absolute value of a first standard score in the first standard score function to calculate a first total, wherein the data collection module standardizes the second lead electrocardiogram into a second standard score function, and selects at least one second standard score from a plurality of second standard scores of the second standard score function in response to at least one second absolute value of the at least one second standard score in the second standard score function being greater than a second absolute value of a second standard score in the second standard score function to calculate a second total, wherein the data collection module selects the electrocardiogram corresponding to a third lead from the plurality of electrocardiograms according to signs of the first total and the second total.

10. The electronic device according to claim 9, wherein the first lead electrocardiogram corresponds to a lead I, wherein the second lead electrocardiogram corresponds to a lead aVF, wherein the third lead corresponds to one of a lead II, a lead aVL, the lead aVF, and a lead aVR.

11. The electronic device according to claim 1, wherein the feature selection module selects the first feature in response to the first performance index being greater than a performance threshold.

12. The electronic device according to claim 1, wherein the feature establishing module calculates a second feature value corresponding to a second feature according to the plurality of extreme points of the at least one type of wave, and generates a second performance index corresponding to the machine learning model according to the second feature value, wherein the feature selection module selects the first feature from the first feature and the second feature in response to the first performance index being greater than the second performance index.

* * * * *